United States Patent
Kreger et al.

[11] Patent Number: 6,070,097
[45] Date of Patent: May 30, 2000

[54] METHOD FOR GENERATING A GATING SIGNAL FOR CARDIAC MRI

[75] Inventors: Kevin S. Kreger, Milwaukee; Sudha Maniam, Menomonee Falls; Kathleen J. Bahner, Lake Mills, all of Wis.; Eric Tzguang Han, Winter Park, Fla.

[73] Assignee: General Electric Company, Milwaukee, Wis.

[21] Appl. No.: 09/223,216

[22] Filed: Dec. 30, 1998

[51] Int. Cl.⁷ .................................................. A61B 5/0456
[52] U.S. Cl. ............................................ 600/521; 600/413
[58] Field of Search ....................................... 600/521, 413

[56] References Cited

U.S. PATENT DOCUMENTS

| | | |
|---|---|---|
| 3,554,187 | 1/1971 | Glassner et al. . |
| 3,590,811 | 7/1971 | Harris . |
| 3,654,916 | 4/1972 | McEwan et al. . |
| 3,707,959 | 1/1973 | Wilton-Davies . |
| 3,861,387 | 1/1975 | Lawhorn . |
| 3,903,874 | 9/1975 | Shakespeare . |
| 3,939,824 | 2/1976 | Arneson et al. . |
| 3,995,624 | 12/1976 | Mass . |
| 3,998,214 | 12/1976 | Garrison . |
| 4,000,461 | 12/1976 | Barber et al. . |
| 4,112,930 | 9/1978 | Feldman et al. . |
| 4,181,135 | 1/1980 | Andresen et al. . |
| 4,259,966 | 4/1981 | Cannon et al. . |
| 4,263,919 | 4/1981 | Levin . |
| 4,630,204 | 12/1986 | Mortara . |
| 4,732,158 | 3/1988 | Sadeh . |
| 5,025,794 | 6/1991 | Albert et al. . |

*Primary Examiner*—Scott M. Getzow
*Attorney, Agent, or Firm*—Quarles & Brady; Christian G. Cabou; Phyllis Y. Price

[57] ABSTRACT

An MRI system includes a detector system which receives an ECG signal from a patient being scanned and produces a gating signal. The gating signal is produced when a detected peak in the ECG signal meets a set of R-wave criteria which includes a specified positive slope on the leading segment of the detected peak, a minimum duration of the leading segment, specified negative slope on the segment trailing the detected peak and a minimum peak amplitude.

10 Claims, 3 Drawing Sheets

METHOD FOR GENERATING A GATING SIGNAL FOR CARDIAC MRI

BACKGROUND OF THE INVENTION

The field of the invention is nuclear magnetic resonance imaging methods and systems. More particularly, the invention relates to the accurate generation of gating signals for use in cardiac gated MR imaging and spectroscopy.

The data required to reconstruct an MR image is acquired by an MRI system over a period of time. In most acquisitions this time period extends over many cardiac cycles of the patient and sometimes it is necessary to synchronize the acquisition with the cardiac cycle. This is accomplished by monitoring an ECG signal produced by the patient's heart and triggering, or gating, the data acquisition sequence when the R-peak in the QRS complex is detected.

The accurate detection of the R-peak in the ECG signal is very difficult in an MRI system environment. First, the quality of the ECG signal itself is seriously degraded by the magnetic induction effects caused by the strong magnetic fields used in MRI systems. Significant inductive noise is added to the ECG signal by patient movement and blood flow as well as "gradient noise" produced by the rapidly changing magnetic field gradients used during all MRI acquisitions.

When used for gating MR data acquisition, the detection and signaling of the R-peak event in the ECG signal must be done on a real-time basis. In a cardiac gated MRI scan, data is acquired over a portion of the cardiac cycle following each ECG gating signal, and it is a major objective to begin acquiring data as soon as possible after the occurrence of the R-peak. Since this acquisition window begins immediately after the QRS complex in the ECG signal, any time delay in producing the gating signal translates to a corresponding reduction in the data acquisition window. Such delays prevent the acquisition of images which depict the heart in the early systolic phase of the cardiac cycle. A delay in excess of 30 milliseconds is unacceptable for many scan types.

The need for a real-time gating signal means that very limited filtering of the noisy ECG signal can be performed. For example, a filter designed to block frequencies above 15 Hz can impose a time delay on the ECG signal of greater than 30 milliseconds. Since this is excessive for MR gating purposes, the R-peak detector must function accurately and consistently with a relatively noisy ECG signal.

R-wave detectors used in the past generally fall into three classes. The first employs a band pass filter and is based on the principle that the QRS complex is rich in 10 to 17 Hz frequency components and that the ECG waveform can be passed through a filter which has a center frequency of about 10 Hz so that the accentuated frequency can be detected. One problem with this approach is that the ECG signal is delayed too long by the filter as discussed above. Another problem with this class of detectors is that patient movement and gradient induced noise may contain components with about the same frequency range so it is difficult for the detector to distinguish them from a true R-wave or QRS complex. Moreover, the QRS portion of the ECG waveform with certain types of heart defects is much wider than the normal or average width for a healthy subject so it is also rich in frequencies lower than the center frequency of the filter which is set for the normal QRS complex.

Another class of R-wave detectors operates on the principle that the slope of the leading and trailing edges of the QRS complex are uniquely different from those of the P and T wave portions of the ECG. The assumption is, therefore, that the derivative of the ECG waveform can be obtained and that when the output exceeds some preset threshold value, the equivalent of some preset slope, that this can be detected. The disadvantage of prior derivative class detectors is that some technique must be used to limit the noise induced by the gradient amplifiers. These gradient induced noise spikes have slopes equal to or greater than that of the QRS complex. Such similar slopes are hard to distinguish from the R-wave slopes. In U.S. Pat. No. 3,939,824 this problem is addressed by requiring that the derivative, or slope, of the ECG signal be maintained above the preset threshold value for a minimum time interval.

A third approach is an amplitude based technique that relies on analyzing the peaks in the ECG signal and setting an amplitude threshold that, when reached, will produce the gating signal. The accuracy of such techniques is highly correlated with the amount of filtering that is used, since high amplitude noise spikes can trigger the detector. In a current system used by the General Electric Company in its MRI systems, a measurement accuracy of 95.4% (i.e. a failure rate of 1 out of 22 R-peaks) is achieved with an amplitude based method that imposes a time delay of approximately 25 milliseconds on the gating signal.

SUMMARY OF THE INVENTION

The present invention is a detector system for producing a real-time gating signal that indicates the occurrence of an R-peak waveform in an ECG signal. More specifically, the detector system includes a segment detector which receives the ECG signal and detects segments therein which have a positive slope, a slope calculator which measures the slope of detected segments; and a comparator which determines if the measured slope of the segment is within a preset range of values and produces a gating signal if it is. Another aspect of the invention is that the unfiltered ECG signal is applied to the segment detector and a filtered version is applied to the slope calculator. The delay imposed by the filter is substantially the same delay requirement of the segment detector and the filtering is performed concurrently with the segment detection.

The present invention improves the measurement accuracy of a cardiac gating system on an MRI system without imposing an additional delay on the gating signal. Segments of the ECG signal having a positive slope for a minimum time interval are detected as candidates for the leading edge of the R-peak in the QRS complex. Increased accuracy is achieved in part by measuring the average slope of the central portion of this detected segment and comparing it with a preset range of values. It has been discovered that the central portion of the leading edge of an R-peak is a more reliable indicator than the entire leading edge.

The invention also provides a detection system which adapts to different patients and to changes that may occur in the ECG signal during the scan. The preset range of values that indicate the slope of the R-peak leading edge is determined by operating the detection system in an initialization mode prior to scanning the patient. In this mode there is no need for real-time operation and slope information can be acquired using highly filtered ECG signals and averaging multiple measurements. During the scan of the patient, the preset range of values may be adjusted using the slope measurements acquired during the real-time mode of operation.

DESCRIPTION OF THE PREFERRED EMBODIMENT

Figure 1:
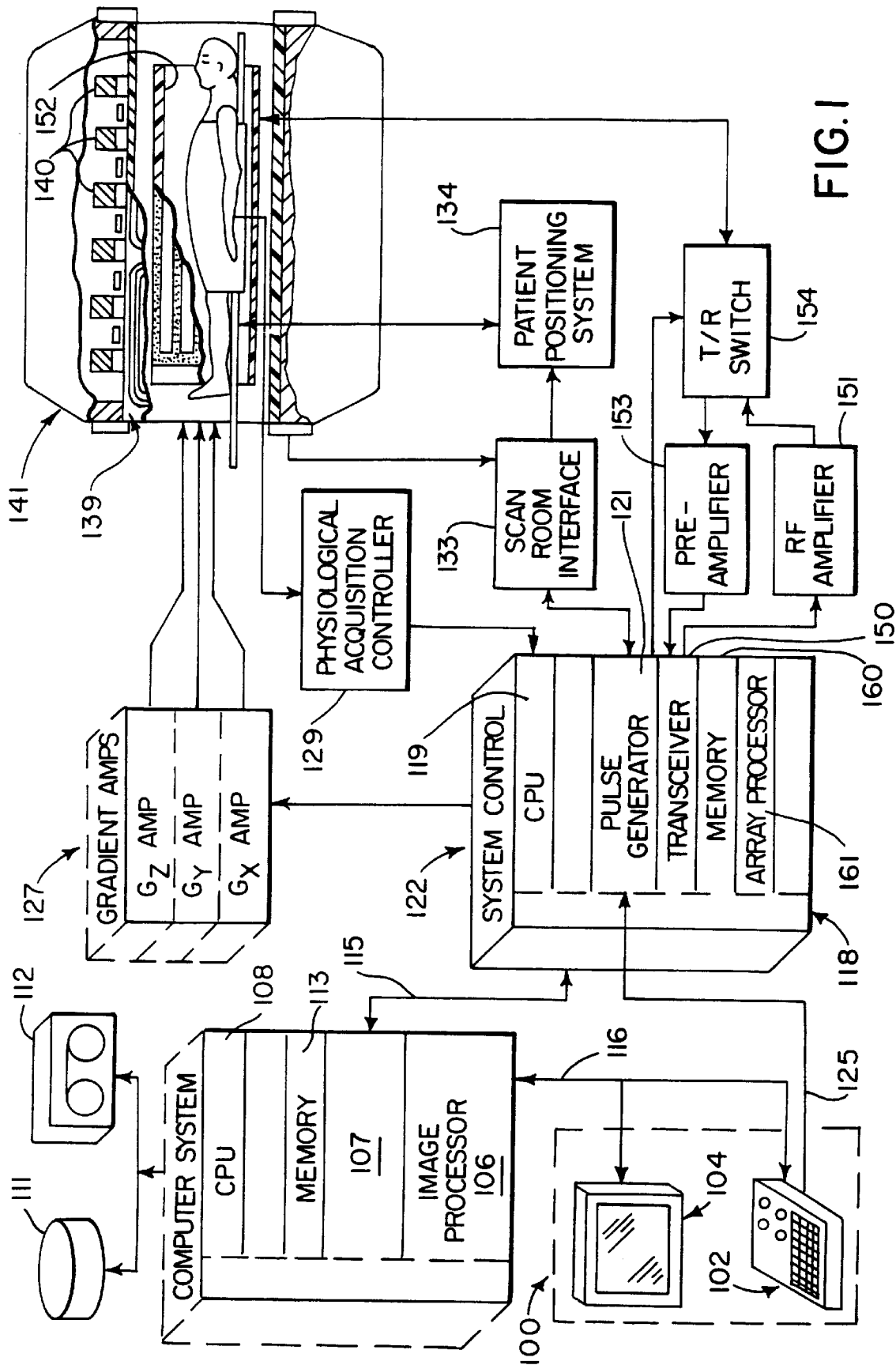
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan.

The system controller 122 receives patient data from a physiological acquisition controller ("PAC") 129 that receives signals ECG signals from sensors connected to the patient. As will be explained in more detail below, an ECG acquisition circuit in the PAC 129 combines and digitizes an ECG signal that is optically coupled to the system controller 122. A detector system analyzes this ECG signal, as will be described in detail below, and produces an ECG trigger signal for the pulse generator module 121.

The pulse generator module 121 also connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,992,736 which are incorporated herein by reference.

Figure 2:
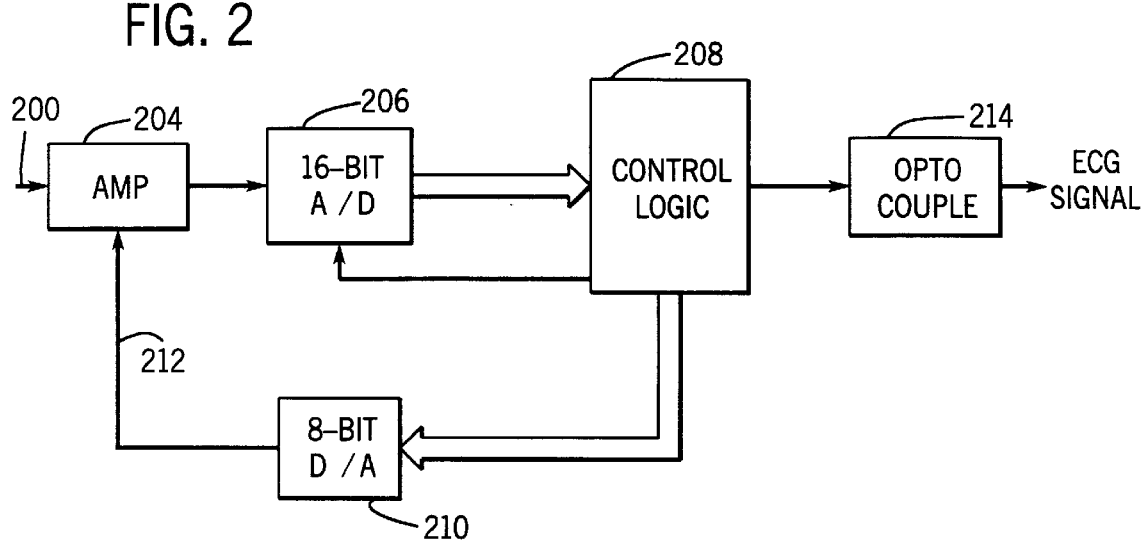
FIG. 2 is a block diagram of an ECG acquisition circuit employed in the MRI system of FIG. 1 to produce an ECG signal.

Referring particularly to FIG. 2, a digitized ECG signal is produced by an ECG acquisition circuit in the physiological acquisition controller 129. This circuit is connected through leads to electrodes (not shown) attached to the patient's chest. A low-level analog differential signal is input at 200 from these electrodes during the cardiac cycle and it is amplified by variable gain amplifier 204 and applied to the input of a 16-bit analog to digital converter 206. The A/D converter 206 is controlled by control logic 208 to sample the amplified analog signal at a rate of 1000 samples per second. The control logic 208 also adjusts the gain of the amplifier 204 to maintain the amplitude of the analog signal well within the range of the A/D converter 206. This is accomplished by outputting gain values to an 8-bit digital to analog converter 210 which controls the gain of amplifier 204 through control line 212.

The resulting ECG signal is a stream of 12-bit digitized samples which are output through an opto coupler 214 to the system control 122 (FIG. 1). The 1 kHz sample rate provides a 500 Hz bandwidth for the ECG signal, which is sufficient to measure the R-peak with an accuracy of 0.5 msecs.

Referring particularly to FIG. 1, the CPU 119 in the system control 122 is programmed to input the ECG signal from the PAC 129 and to output an ECG trigger signal to the pulse generator module 121 each time the peak in the R-wave is detected. The function performed by this detector system is shown in the flow chart of FIG. 3.

Figure 4:
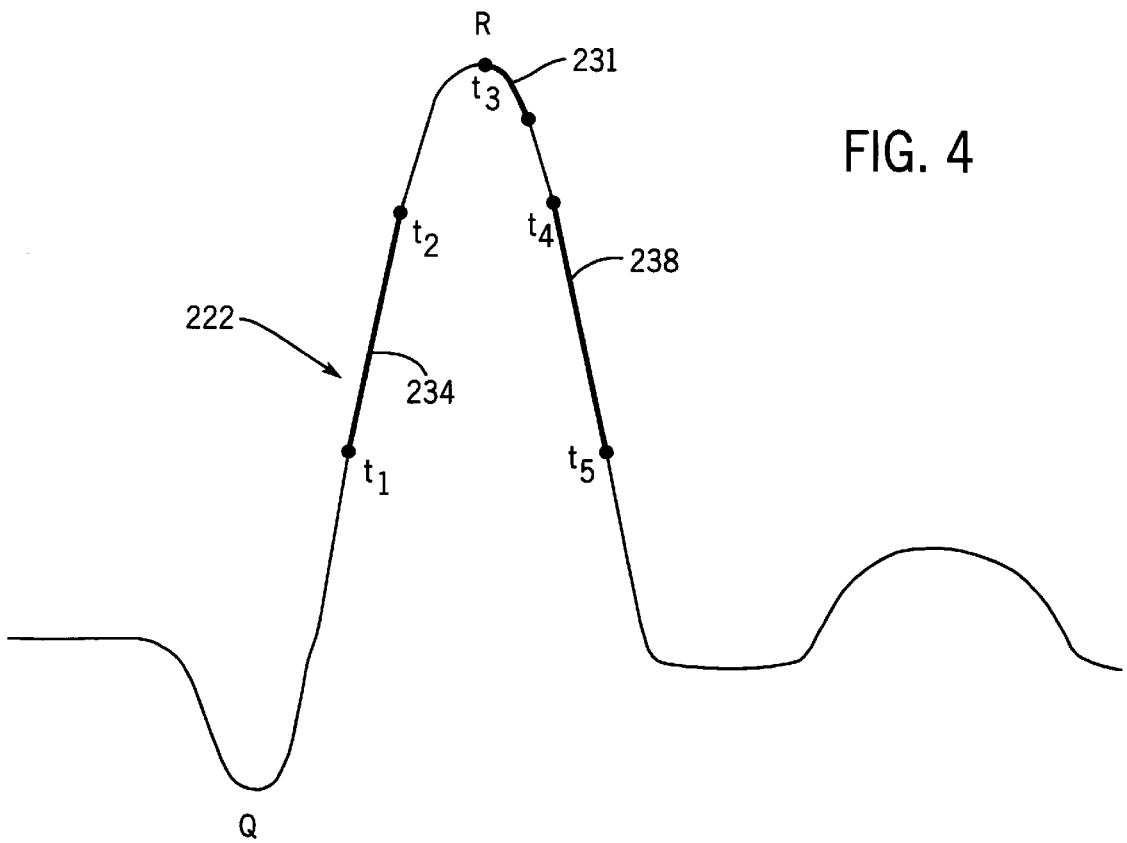
FIG. 4 is a graphic representation of an exemplary ECG signal analyzed by the detector system of FIG. 3.
Figure 3:
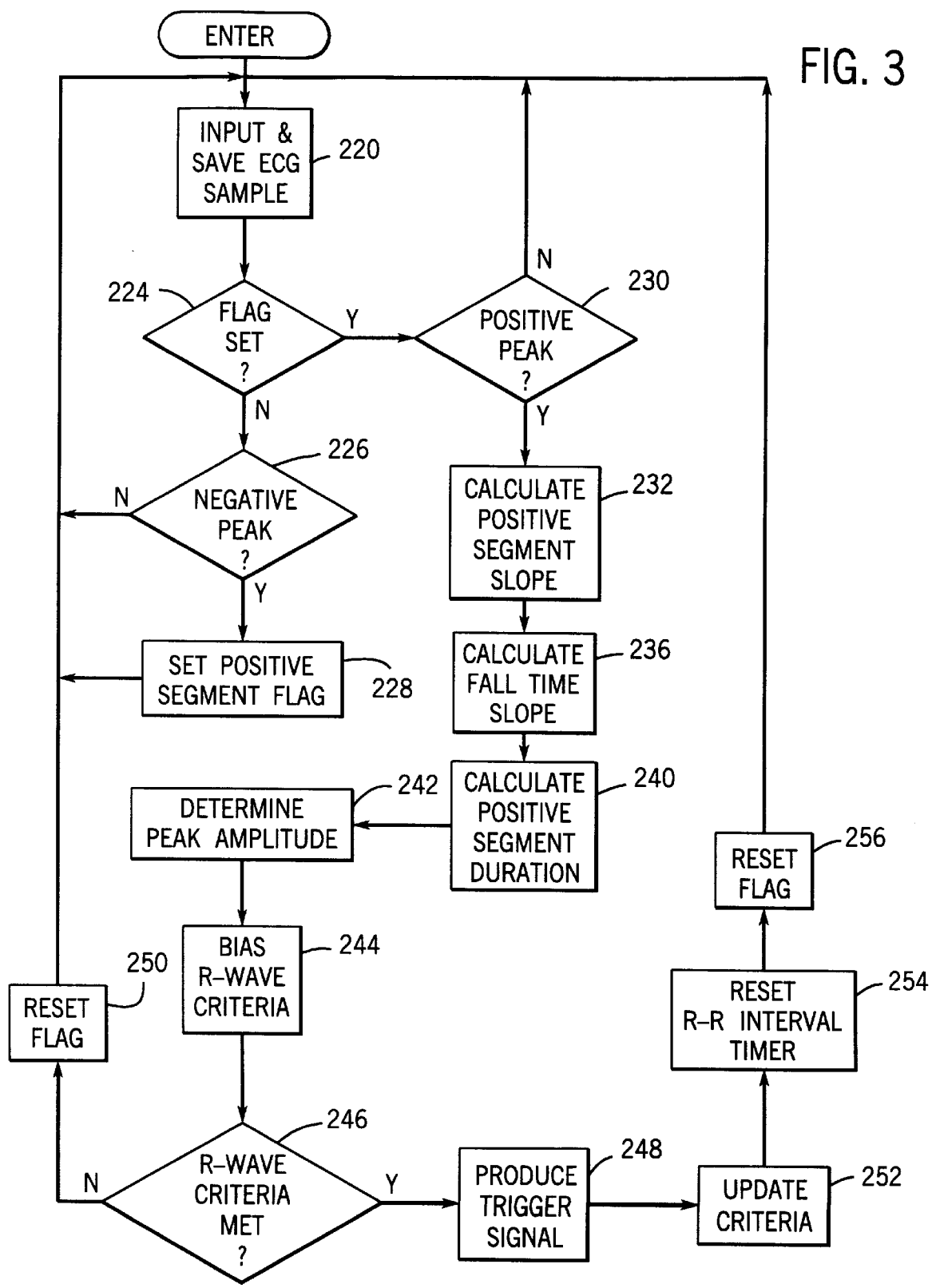
FIG. 3 is a flow chart of the functions performed by a detector system which forms part of the MRI system of FIG. 1.

Referring particularly to FIG. 3, the ECG signal sample is input at process block 220 and saved in a FIFO memory data structure (not shown). As will become apparent below, the ECG signal data is analyzed to determine if a true R-peak has been detected, and the most current 50 milliseconds of ECG signal data is saved in the FIFO memory structure for this purpose. Referring to FIG. 4, an important aspect of the present invention is to detect the QR signal segment 222 that occurs just following the negative peak of the Q-wave. The QR segment is detected by testing or a negative peak in the sampled ECG signal, and when one is detected, positive segment flag is set. The sampling continues until the positive R-peak is detected, and at that point the ECG samples stored in the FIFO memory are analyzed to determine if a true R-wave peak has been detected as determined by a set of stored criteria. If the R-peak is confirmed, an ECG trigger signal is generated. In either case, the positive segment flag is reset and the process repeats. Another data structure used by the detection system is an R—R interval timer which indicates the elapsed time since the prior R-peak detection event. As will be explained in more detail below, this elapsed time is employed to modify the criteria used to determine if an R-peak has been detected.

Referring again to FIGS. 3 and 4, after an ECG sample is input at process block 220 the positive segment flag is checked at decision block 224 to determine if a negative peak has already been detected. If not, a determination is made at decision block 226 as to whether a negative peak has been detected. This is accomplished by comparing the amplitude of the last ECG sample stored in the FIFO memory to determine if it is greater than previous signal samples by a preset amount. If so, a negative peak in the ECG signal has occurred and the positive segment flag is set as indicated by process block 228.

If the positive segment flag is set when a signal sample is received, the system tests to determine if the end of the positive segment has been reached. There is accomplished at decision block 230 by detecting a positive peak in the most recently stored ECG signal samples. In the preferred embodiment this is done by determining if the most recent signal samples have dropped below the amplitude of a previous signal sample for a preset amount of time. In the preferred embodiment this preset time is 4 msecs. as indicated in FIG. 4 at 231.

If the positive peak is detected, the stored signal samples are analyzed to determine if the peak qualifies as an R-wave peak. As indicated by process block 232, the first step in the analysis is to calculate the slope of the positive signal segment to determine if it meets the criteria for a QR segment. As shown in FIG. 4, only the most linear central portion 234 of the positive segment is used for this calculation. Signal samples on the curved portions before the sample at $t_1$ and after the sample at $t_2$ are excluded from the slope calculation. To reduce processing time, the positive slope is calculated by averaging the difference in amplitude between successive samples acquired between $t_1$ and $t_2$. It has been discovered that this average rate of rise, or slope, is a good indicator of the leading edge of the R-wave.

As indicated in FIG. 3, the next step at process block 236 is to calculate the slope of the ECG signal following the positive peak. This following signal segment 238 between times $t_4$ and $t_5$ includes samples on the downslope of the R-wave which correspond roughly with those in the signal segment 234. As with the positive slope calculation, this negative slope calculation is performed by averaging the amplitude difference between successive signal samples in the segment 238. It has been discovered that accuracy of the R-peak detection is increased if the slope of this falling signal segment 238 is within preset limits. However, it is also possible as an alternative embodiment in some scans to eliminate this step.

The next steps indicated at process blocks 240 and 242 is to calculate the time duration of the positive segment 222 and the amplitude of the ECG signal at the peak sample $t_3$. The duration is calculated by simply summing the number of ECG signal samples acquired during the positive slope segment 222 and the peak amplitude is read from the appropriate location in the FIFO memory structure. These values are now used to determine if the acquired positive peak is the R-wave of the patient's ECG signal. The values for positive slope, negative slope, segment duration and peak amplitude are compared with corresponding stored limits that define the criteria for the patient's R-wave. As will be explained in detail below, these values are determined during an initialization mode of operation and they are updated during the scan.

These criteria are not a fixed standard, and their values are biased as a function of the elapsed time since detection of the previous R-wave as indicated at process block 244. More specifically, the R—R interval timer which indicates elapsed time since the previous ECG trigger is compared with an average R—R interval that is maintained by the detector system. If the candidate event occurs within the first 20% of the average R—R interval, the R-wave event is viewed as highly unlikely and the R-Wave criteria is biased very narrowly. The candidate event must be very close in slopes, duration and amplitude to the averages in order to meet the R-wave criteria. For example, the QR segment slope must be within 0.001 of the criteria. If the candidate event occurs within the first 50% of the average R—R interval, the criteria are relaxed by setting a range for each criteria equal to one-half the full range. If the candidate event occurs beyond 50% of the average R—R interval, the criteria are relaxed further by increasing the ranges by 20%.

As indicated by decision block 246, if the measured values are within the allowed ranges of values, the R-wave criteria are met and an ECG trigger signal is produced as indicated by process block 248. If the candidate event does not meet the R-wave criteria, the positive segment flag is reset at process block 250 and the system loops back to continue searching for the next R-wave.

After the ECG trigger signal is produced a number of functions are performed before the system loops back to search for the next R-wave. One task is to update the R-wave criteria as indicated at process block 252. This includes changing the stored average values for the positive segment duration and the peak amplitude to reflect the actual values just measured for the R-wave event. This is done utilizing a weighted moving averager.

The next step is to reset the R—R interval timer to reflect the start of another interval as indicated at process block 254. In addition, the average R—R interval value is updated to include the duration of the R—R interval just concluded. The updated average is calculated by averaging the last four non-arrhythmic R—R intervals. The positive segment flag is then reset at process block 256 and the system loops back to search for the next R-wave event.

The detector system has been found to trigger accurately 99.19% of the time. This is a failure rate of about 1 out of every 100 R-waves. In addition, this accuracy is achieved without imposing an additional delay on the ECG trigger signal. The peak detection steps are performed with unfiltered digital ECG samples such that there is minimal delay between detection of the R-wave peak and generation of the ECG trigger signal. Nevertheless, the ECG samples stored in the FIFO memory can be filtered for slope measurement without delaying the detection process because the filtering can take place before the detection of the R-peak using the unfiltered ECG signal. As a result, the slopes can be calculated using a less noisy signal.

The criteria used to determine if a candidate event is an R-wave is determined for each patient during an initialization procedure. No image data is acquired during this initialization procedure and delay in detecting the R-wave peak is of no concern. Therefore, the ECG signal is filtered to reduce noise and improve accuracy. During initialization mode the detector system triggers utilizing an amplitude threshold. The amplitude threshold is set so as to produce preliminary triggers on the rising QR segment (before the actual R-peak occurs). This trigger arms the peak detector which then looks for a sustained drop in the ECG signal. At this point the R-peak has elapsed and a slope measurement is performed on the filtered QR segment data. This slope measurement carefully avoids data points near the apex of the peak by averaging the slope over a flatter interior portion of the isolated segment. This slope measurement is accepted by the estimator if it is both close to the previous slope measurements and the QR segment has a minimum number of data points. If these criteria are met the slope and amplitude of the QR segment are retained. This process continues until enough slope and amplitude measurements are acquired and retained to estimate the average slope and amplitude of the patient's QR segment. The estimate is an average of these collected values with the highest and the lowest value eliminated.

What is claimed is:

1. In an MRI system which acquires image data from a subject, a method for producing a cardiac gating signal which comprises:
   a) producing an ECG signal which includes periodic R-waves that indicate the patient's cardiac cycle;
   b) detecting a positive slope segment in the ECG signal;
   c) detecting the peak in the ECG signal at the end of the detected positive slope segment; and
   d) producing a cardiac gating signal if the detected peak satisfies R-wave criteria which includes:
      calculating the slope of the detected positive slope segment and determining if the slope is within a specified range of valve.

2. The method as recited in claim 1 in which the R-wave criteria also includes:
   determining the duration of the detected positive slope segment and determining if it exceeds a specified duration value.

3. The method as recited in claim 2 in which the R-wave criteria also includes:
   calculating the negative slope of a segment of the ECG signal following the detected peak and determining if the negative slope is within a specified range of negative slope values.

4. The method as recited in claim 3 in which the R-wave criteria also includes:
   determining the amplitude of the ECG signal at the detected peak and determining if it exceeds a specified amplitude value.

5. The method as recited in claim 1 which includes:
   establishing an R—R interval which is indicative of the average time between R-waves in the ECG signal; and
   biasing the R-wave criteria as a function of when in the R—R interval said peak is detected, such that the range of values is greater when the peak is detected closer to the R—R interval.

6. The method as recited in claim 1 in which step b) is performed by detecting a negative peak in the ECG signal.

7. The method as recited in claim 1 in which the slope of the detected positive slope segment is calculated using only a central portion of the detected positive slope segment.

8. The method as recited in claim 7 in which the ECG signal is comprised of periodic digital samples, and the slope is calculated by averaging the change in amplitude of successive digital samples.

9. The method as recited in claim 1 in which the detected positive slope segment of the ECG signal is filtered before calculating its slope.

10. The method as recited in claim 1 in which the ECG signal is comprised of periodic digital samples and step c) is performed by detecting a reduction in the amplitude of successive digital samples.

* * * * *